(12) United States Patent
Ke et al.

(10) Patent No.: US 11,642,016 B2
(45) Date of Patent: May 9, 2023

(54) IMAGE CAPTURING MODULE, ENDOSCOPE AND METHOD OF MANUFACTURING IMAGE CAPTURING MODULE

(71) Applicant: ALTEK BIOTECHNOLOGY CORPORATION, Hsinchu (TW)

(72) Inventors: Ting-Cheng Ke, Hsinchu (TW); Chao-Yu Chou, Hsinchu (TW); Po-Ju Chen, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 0 days.

(21) Appl. No.: 17/399,027

(22) Filed: Aug. 10, 2021

(65) Prior Publication Data

US 2023/0048452 A1 Feb. 16, 2023

(51) Int. Cl.
| | |
|---|---|
| *A61B 1/05* | (2006.01) |
| *A61B 1/07* | (2006.01) |
| *A61B 1/00* | (2006.01) |
| *A61B 1/06* | (2006.01) |
| *H04N 23/54* | (2023.01) |

(Continued)

(52) U.S. Cl.
CPC ............ *A61B 1/051* (2013.01); *A61B 1/0011* (2013.01); *A61B 1/0676* (2013.01); *A61B 1/07* (2013.01); *H04N 23/54* (2023.01); *H04N 23/56* (2023.01); *H04N 23/555* (2023.01)

(58) Field of Classification Search
CPC ....... A61B 1/0011; A61B 1/041; A61B 1/051; A61B 1/0676; A61B 1/0684; A61B 1/07; H05K 1/118; H05K 1/189; H05K 2201/055; H05K 2201/056; H05K 2201/10106; H05K 2201/10121; H05K 1/028; H05K 1/0281; H05K 1/147; H05K 2201/058; H04N 23/54

See application file for complete search history.

(56) References Cited

U.S. PATENT DOCUMENTS 5,857,963 A * 1/1999 Pelchy ................. H04N 5/2253
600/109
11,153,970 B1 * 10/2021 Smith ................... A61B 1/0676
(Continued)

FOREIGN PATENT DOCUMENTS

| EP | 2 744 386 B1 | 12/2018 |
|---|---|---|
| EP | 2 996 557 B1 | 5/2019 |
| TW | M576855 U | 4/2019 |

*Primary Examiner* — Aaron B Fairchild
*Assistant Examiner* — Stephen Floyd London
(74) *Attorney, Agent, or Firm* — Winston Hsu (57) ABSTRACT

An image capturing module includes a flexible circuit board and an image sensor. The flexible circuit board includes a plurality of first pads and a plurality of second pads. The first pads are disposed on a first surface of the flexible circuit board and the second pads are disposed on a second surface of the flexible circuit board, wherein the first surface is opposite to the second surface. The image sensor is disposed on the first surface. A distance between the image sensor and the first pads is identical to a distance between the image sensor and the second pads. The flexible circuit board is folded to align and weld the first pads with the second pads, such that a light receiving surface of the image sensor is perpendicular to surfaces of the first and second pads.

20 Claims, 11 Drawing Sheets

(51) Int. Cl.
   *H04N 23/56* (2023.01)
   *H04N 23/50* (2023.01)

(56) References Cited

U.S. PATENT DOCUMENTS

| | | | | |
|---|---|---|---|---|
| 2009/0268019 | A1* | 10/2009 | Ishii | G03B 17/02 |
| | | | | 348/294 |
| 2011/0295064 | A1* | 12/2011 | Kagawa | A61B 1/04 |
| | | | | 600/110 |
| 2013/0303849 | A1* | 11/2013 | Allyn | A61J 15/0069 |
| | | | | 600/109 |
| 2014/0009593 | A1* | 1/2014 | Segi | A61B 1/04 |
| | | | | 29/745 |
| 2014/0371530 | A1* | 12/2014 | Wieters | G02B 23/2476 |
| | | | | 600/109 |
| 2015/0228678 | A1* | 8/2015 | Yoshida | H01L 27/1464 |
| | | | | 600/110 |
| 2015/0378144 | A1* | 12/2015 | Handte | G02B 23/2484 |
| | | | | 250/208.1 |
| 2017/0251913 | A1* | 9/2017 | Birnkrant | H05K 1/189 |
| 2018/0070803 | A1* | 3/2018 | Mikami | A61B 1/051 |
| 2019/0089875 | A1* | 3/2019 | Fan | H04N 5/2253 |
| 2019/0150711 | A1* | 5/2019 | Chiu | A61B 1/04 |
| 2020/0022571 | A1* | 1/2020 | Kohno | A61B 1/00193 |
| 2020/0297186 | A1 | 9/2020 | Chiu | |
| 2020/0375443 | A1 | 12/2020 | Kwon | |
| 2021/0052134 | A1* | 2/2021 | Chen | A61B 1/0055 |
| 2021/0068640 | A1 | 3/2021 | Sørensen | |
| 2021/0068641 | A1 | 3/2021 | Sørensen | |
| 2021/0127953 | A1* | 5/2021 | Oyama | A61B 1/0011 |
| 2021/0247604 | A1* | 8/2021 | Endo | A61B 1/051 |
| 2021/0249393 | A1* | 8/2021 | Wu | A61B 1/0011 |

* cited by examiner

IMAGE CAPTURING MODULE, ENDOSCOPE AND METHOD OF MANUFACTURING IMAGE CAPTURING MODULE

BACKGROUND OF THE INVENTION

1. Field of the Invention

The invention relates to an image capturing module and, more particularly, to an image capturing module adapted to an endoscope and a method of manufacturing the image capturing module.

2. Description of the Prior Art

Endoscope is a medical instrument that enters a human body through various channels to observe internal conditions of the human body. In general, the endoscope comprises an elongated tube for being inserted into the human body and an image sensor disposed in the elongated tube for capturing inside images of the human body. The thicker the tube is, the more uncomfortable the human body feels. To reduce the thickness of the tube, a micro image sensor has been developed. The micro image sensor is disposed in the elongated tube by a flexible circuit board. However, it is difficult to dispose such a micro image sensor with small dimensions (e.g. 650 μm*650 μm*1158 μm) on a corresponding flexible circuit board.

SUMMARY OF THE INVENTION

The invention provides an image capturing module adapted to an endoscope and a method of manufacturing the image capturing module, so as to solve the aforesaid problems.

According to an embodiment of the invention, an image capturing module comprises a flexible circuit board and an image sensor. The flexible circuit board comprises a plurality of first pads and a plurality of second pads. The first pads are disposed on a first surface of the flexible circuit board and the second pads are disposed on a second surface of the flexible circuit board, wherein the first surface is opposite to the second surface. The image sensor is disposed on the first surface. A distance between the image sensor and the first pads is identical to a distance between the image sensor and the second pads. The flexible circuit board is folded to align and weld the first pads with the second pads, such that a light receiving surface of the image sensor is perpendicular to surfaces of the first and second pads.

According to another embodiment of the invention, an endoscope comprises a tube and an image capturing module. The image capturing module is disposed in the tube. The image capturing module comprises a flexible circuit board and an image sensor. The flexible circuit board comprises a plurality of first pads and a plurality of second pads. The first pads are disposed on a first surface of the flexible circuit board and the second pads are disposed on a second surface of the flexible circuit board, wherein the first surface is opposite to the second surface. The image sensor is disposed on the first surface. A distance between the image sensor and the first pads is identical to a distance between the image sensor and the second pads. The flexible circuit board is folded to align and weld the first pads with the second pads, such that a light receiving surface of the image sensor is perpendicular to surfaces of the first and second pads.

According to another embodiment of the invention, a method of manufacturing an image capturing module comprises steps of forming a plurality of first pads and a plurality of second pads on a flexible circuit board, wherein the first pads is disposed on a first surface of the flexible circuit board, the second pads is disposed on a second surface of the flexible circuit board, and the first surface is opposite to the second surface; disposing an image sensor on the first surface, wherein a distance between the image sensor and the first pads is identical to a distance between the image sensor and the second pads; folding the flexible circuit board to align the first pads with the second pads and make a light receiving surface of the image sensor perpendicular to surfaces of the first and second pads; and welding the first pads with the second pads.

As mentioned in the above, the invention disposes the image sensor on the flexible circuit board first and then folds the flexible circuit board to weld the first pads with the second pads thereon. At this time, the light receiving surface of the image sensor is perpendicular to surfaces of the first and second pads. Accordingly, the folded flexible circuit board with the image sensor can be directly inserted into an elongated tube to form an endoscope, such that the method of manufacturing the endoscope can be simplified and the flexible circuit board of the invention can be used for installing a micro image sensor with small dimensions.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
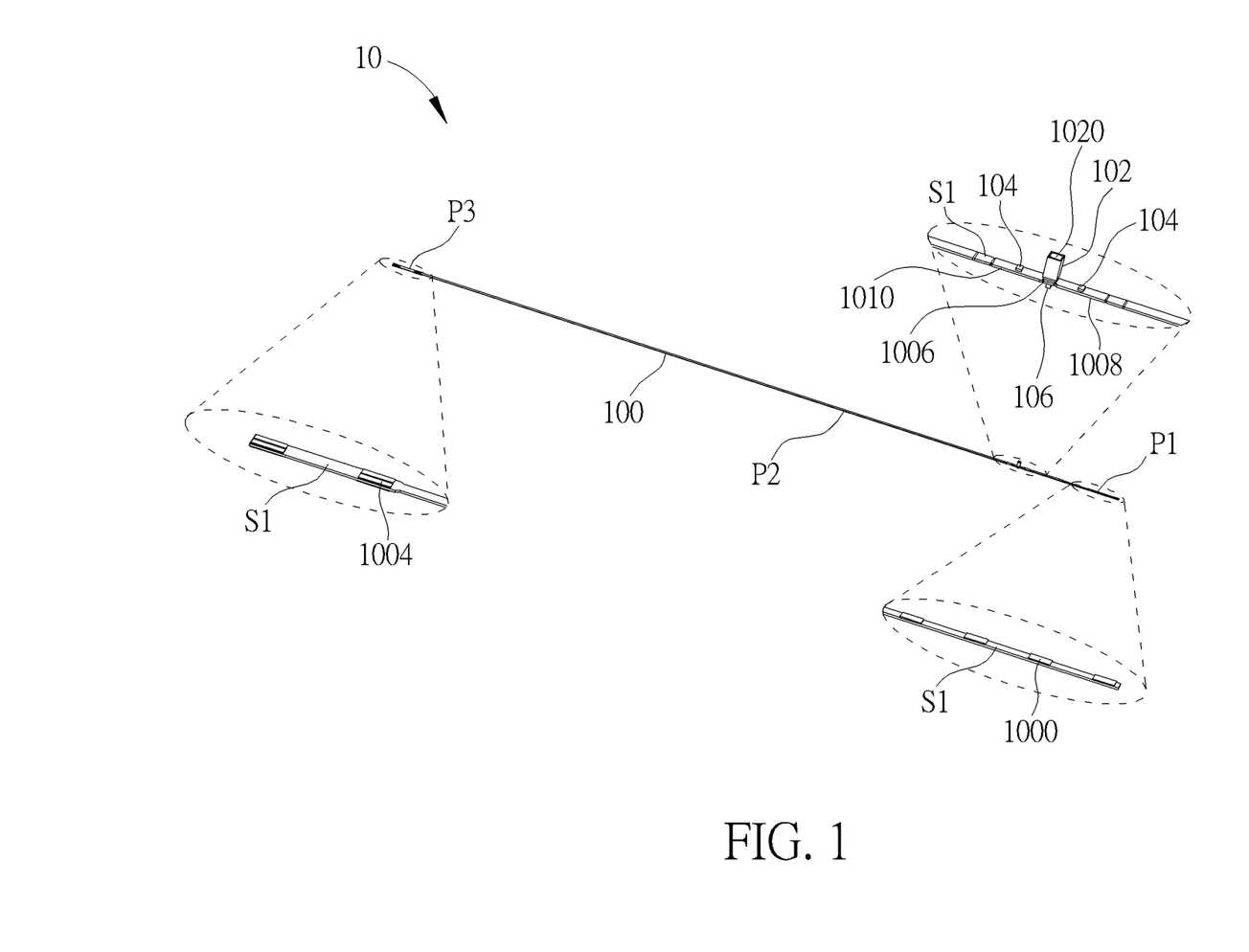
FIG. 1 is a perspective view illustrating an image capturing module before being folded according to an embodiment of the invention.
Figure 2:
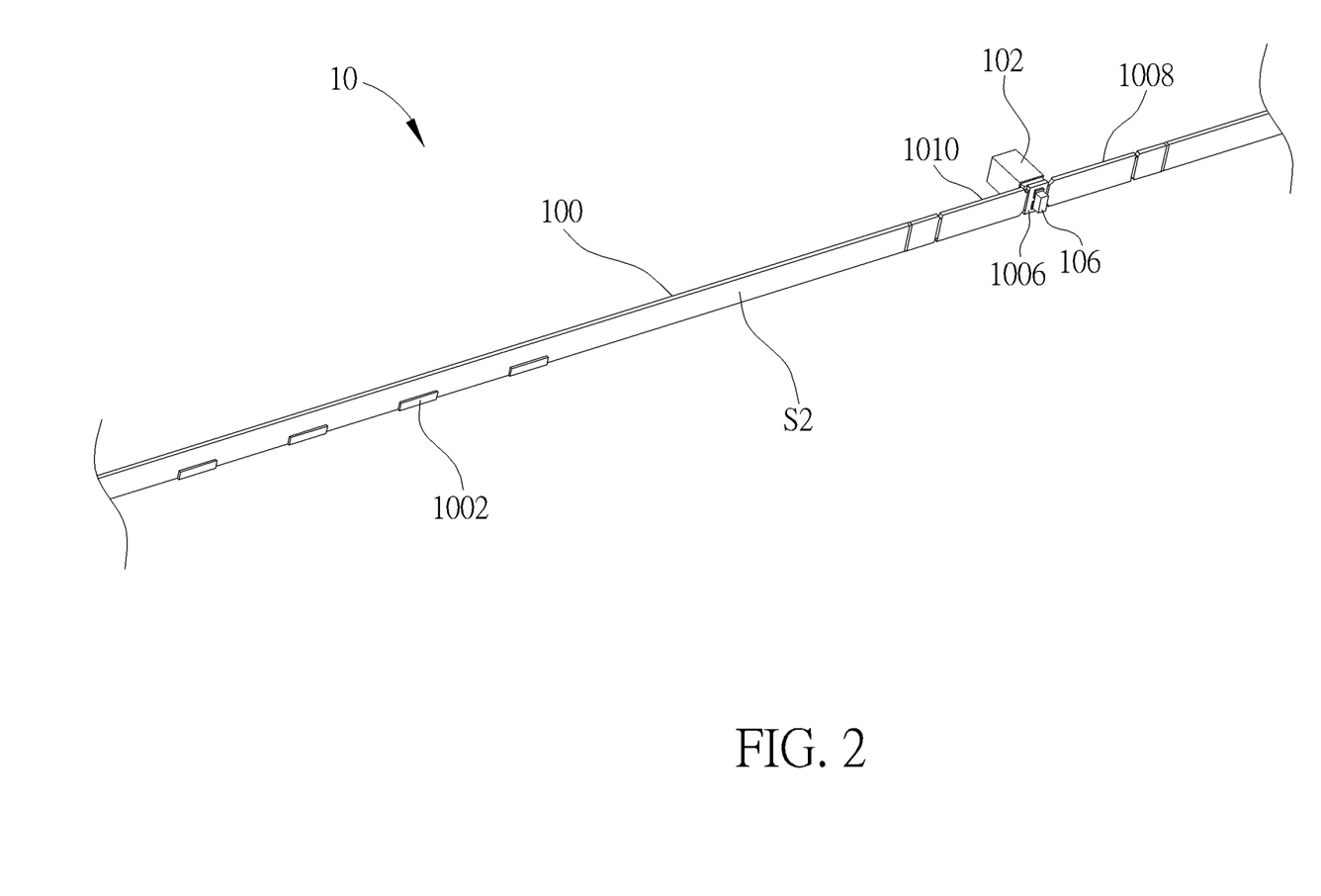
FIG. 2 is a perspective view illustrating parts of the image capturing module shown in FIG. 1 from another viewing angle.
Figure 3:
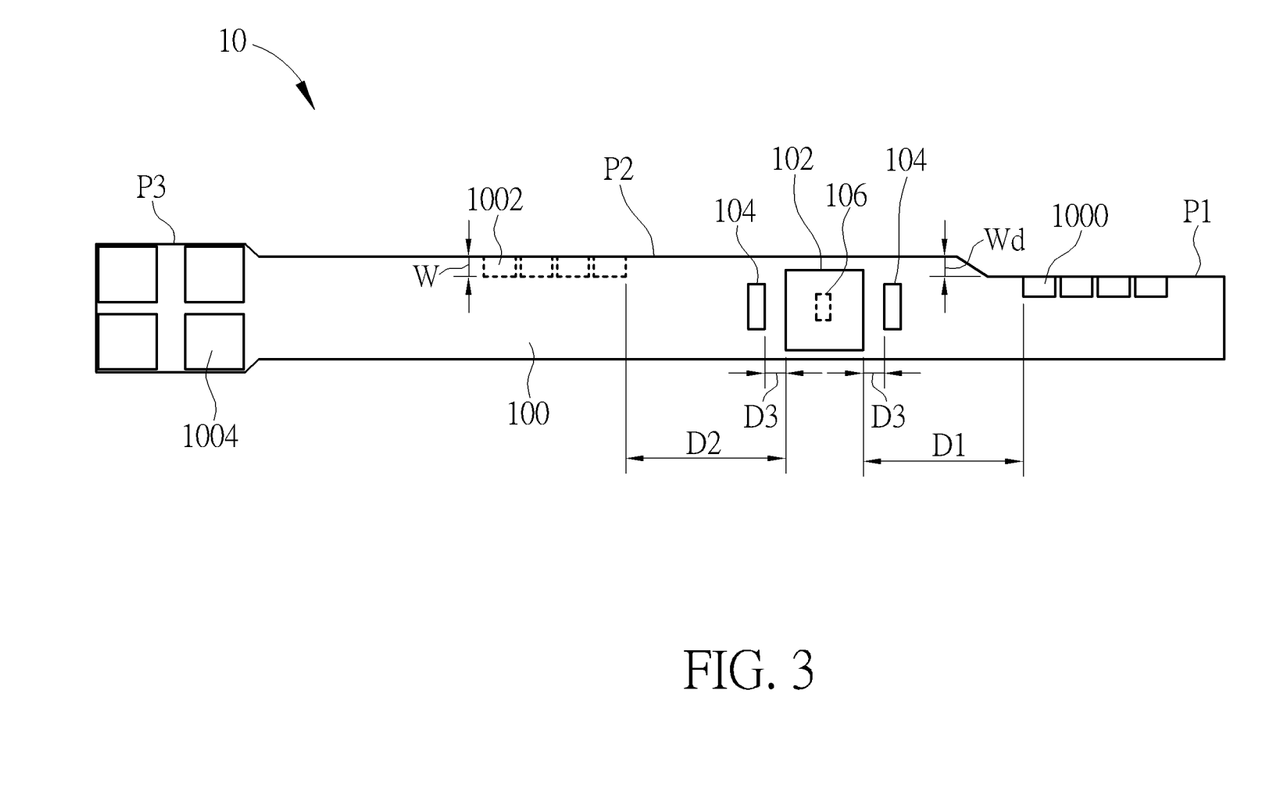
FIG. 3 is a schematic view illustrating the image capturing module shown in FIG. 1.
Figure 4:
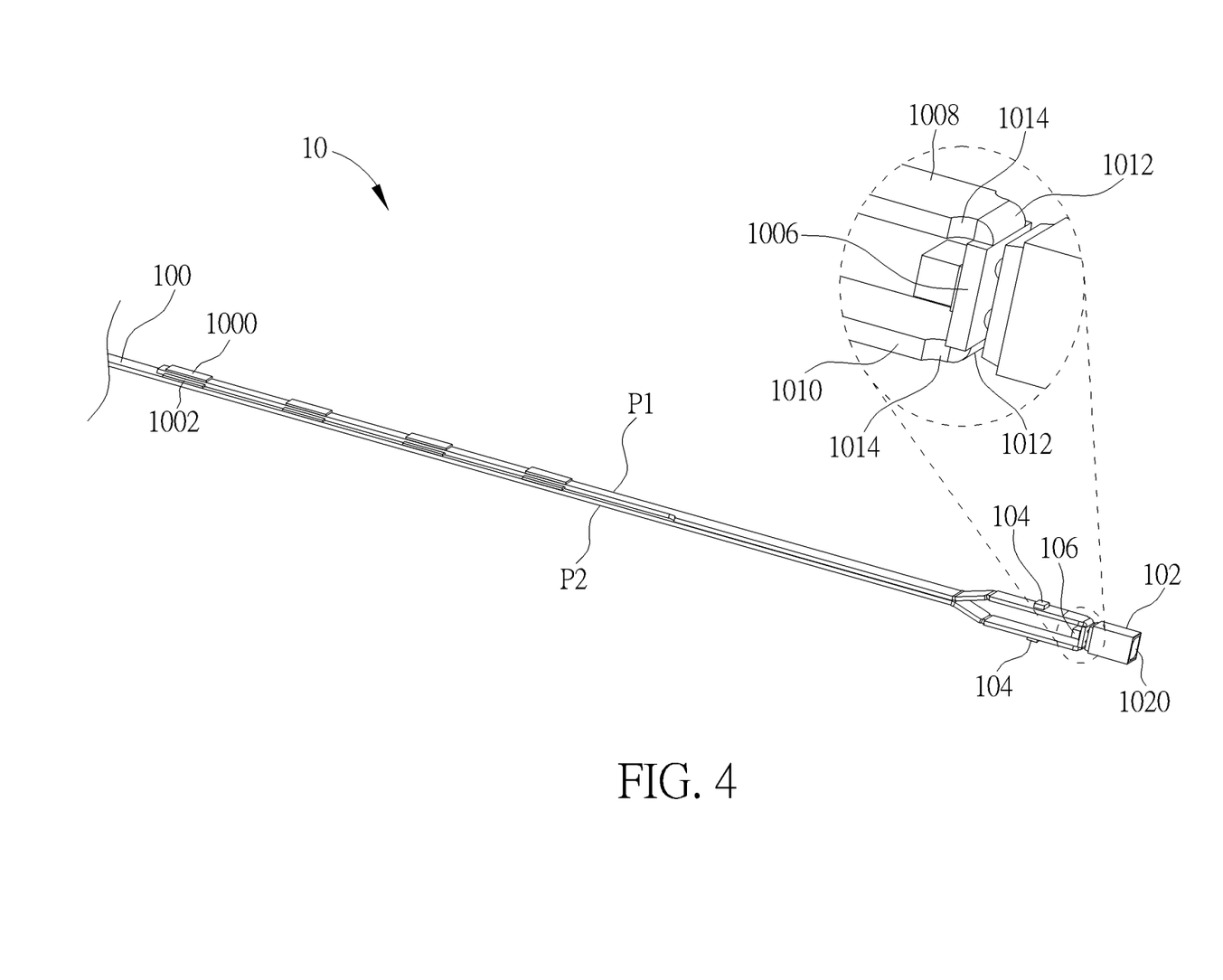
FIG. 4 is a perspective view illustrating parts of the image capturing module shown in FIG. 1 after being folded.

Referring to FIGS. 1 to 4, FIG. 1 is a perspective view illustrating an image capturing module 10 before being folded according to an embodiment of the invention, FIG. 2 is a perspective view illustrating parts of the image capturing module 10 shown in FIG. 1 from another viewing angle, FIG. 3 is a schematic view illustrating the image capturing module 10 shown in FIG. 1, and FIG. 4 is a perspective view illustrating parts of the image capturing module 10 shown in FIG. 1 after being folded.

As shown in FIGS. 1 to 3, an image capturing module 10 before being folded comprises a flexible circuit board 100, an image sensor 102, at least one light emitting unit 104 and at least one electrical component 106. In this embodiment, the flexible circuit board 100 may be a flexible printed circuit board or other flexible circuit boards, the image sensor 102 may be a charge coupled device (CCD) image sensor, a complementary metal oxide semiconductor (CMOS) image sensor or other image sensors, the light emitting unit 104 may be a light emitting diode or other light emitting components, and the electrical component 106 may be a capacitor or other electrical components.

The flexible circuit board 100 comprises a plurality of first pads 1000, a plurality of second pads 1002 and a plurality of third pads 1004. In this embodiment, the flexible circuit board 100 may comprise four first pads 1000, four second pads 1002 and four third pads 1004, but the invention is not so limited. The number of the first pads 1000, the second pads 1002 and the third pads 1004 may be determined according to practical applications.

The first pads 1000 may be disposed on a first surface S1 of the flexible circuit board 100 and the second pads 1002 may be disposed on a second surface S2 of the flexible circuit board 100, wherein the first surface S1 is opposite to the second surface S2. For further illustration, one of the first surface S1 and the second surface S2 may be au upper surface of the flexible circuit board 100, and the other one of the first surface S1 and the second surface S2 may be a lower surface of the circuit board 100.

In this embodiment, the first pads 1000 may be located at a first portion P1 of the flexible circuit board 100, the second pads 1002 may be located at a second portion P2 of the flexible circuit board 100, and the third pads 1004 may be located at a third portion P3 of the flexible circuit board 100, wherein the second portion P2 is connected to the first portion P1 and the third portion P3 is connected to the second portion P2. In other words, the second portion P2 is connected between the first portion P1 and the third portion P3.

In this embodiment, the first pads 1000 are wider than the second pads 1002. As shown in FIG. 3, the second portion P2 may be wider than the first portion P1 and a width W of the second pads P2 may be equal to a width difference Wd between the first portion P1 and the second portion P2. Furthermore, the third portion P3 may be wider than the second portion P2. The third pads 1004 are used for connecting a cable (not shown). Therefore, the wider the third portion P3 is, the easier the cable can be welded with the third pads 1004.

The image sensor 102 is disposed on the first surface S1 of the flexible circuit board 100, wherein a distance D1 between the image sensor 102 and the first pads 1000 is identical to a distance D2 between the image sensor 102 and the second pads 1002, as shown in FIG. 3. In other words, before the flexible circuit board 100 is folded, the image sensor 102 is located at a middle position between the first pads 1000 and the second pads 1002. In this embodiment, the image sensor 102 may be connected to the first surface S1 of the flexible circuit board 100 by surface mount technology (SMT), but the invention is not so limited.

In this embodiment, the image capturing module 10 may comprise two light emitting units 104, but the invention is not so limited. The light emitting units 104 are disposed on the first surface S1 of the flexible circuit board 100, wherein a distance D3 between the image sensor 102 and each of the light emitting units 104 is smaller than the distance D1 or D2 between the image sensor 102 and the first or second pads 1000, 1002, as shown in FIG. 3. That is to say, the light emitting units 104 are closer to the image sensor 102 than the first or second pads 1000, 1002.

In this embodiment, the image capturing module 10 may comprise one electrical component 106, but the invention is not so limited. The electrical component 106 may be disposed on the second surface S2 of the flexible circuit board 100 with respect to the image sensor 102. In other words, the image sensor 102 and the electrical component 106 are disposed on opposite surfaces of the flexible circuit board 100.

In this embodiment, the flexible circuit board 100 may comprises a first folding segment 1006, a second folding segment 1008 and a third folding segment 1010, wherein the first folding segment 1006 is connected between the second folding segment 1008 and the third folding segment 1010. The image sensor 102 and the electrical component 106 is located at opposite surfaces of the first folding segment 1006, and the two light emitting units 104 are respectively located at the second folding segment 1008 and the third folding segment 1010. It should be noted that, in another embodiment, the image capturing module 10 may comprise one light emitting unit 104 located at one of the second folding segment 1008 and the third folding segment 1010. Accordingly, the image capturing module 10 may comprise at least one light emitting unit 104 located at at least one of the second folding segment 1008 and the third folding segment 1010.

In this embodiment, the image sensor 102, the light emitting units 104 and the electrical component 106 may be connected to the flexible circuit board 100 by surface mount technology (SMT) in one process. Then, as shown in FIG. 4, the flexible circuit board 100 is folded to align and weld the first pads 1000 with the second pads 1002, such that a light receiving surface 1020 of the image sensor 102 is perpendicular to surfaces of the first and second pads 1000, 1002. After the flexible circuit board 100 is folded, the first portion P1 is superimposed on the second portion P2, the first folding segment 1006 is perpendicular to the second folding segment 1008 and the third folding segment 1010, and the second folding segment 1008 and the third folding segment 1010 are parallel to each other. Furthermore, joints 1012 between the first folding segment 1006, the second folding segment 1008 and the third folding segment 1010 have rounded recess structures 1014. Accordingly, the first folding segment 1006, the second folding segment 1008 and the third folding segment 1010 may be folded at the joints 1012 according to the rounded recess structures 1014.

Figure 5:
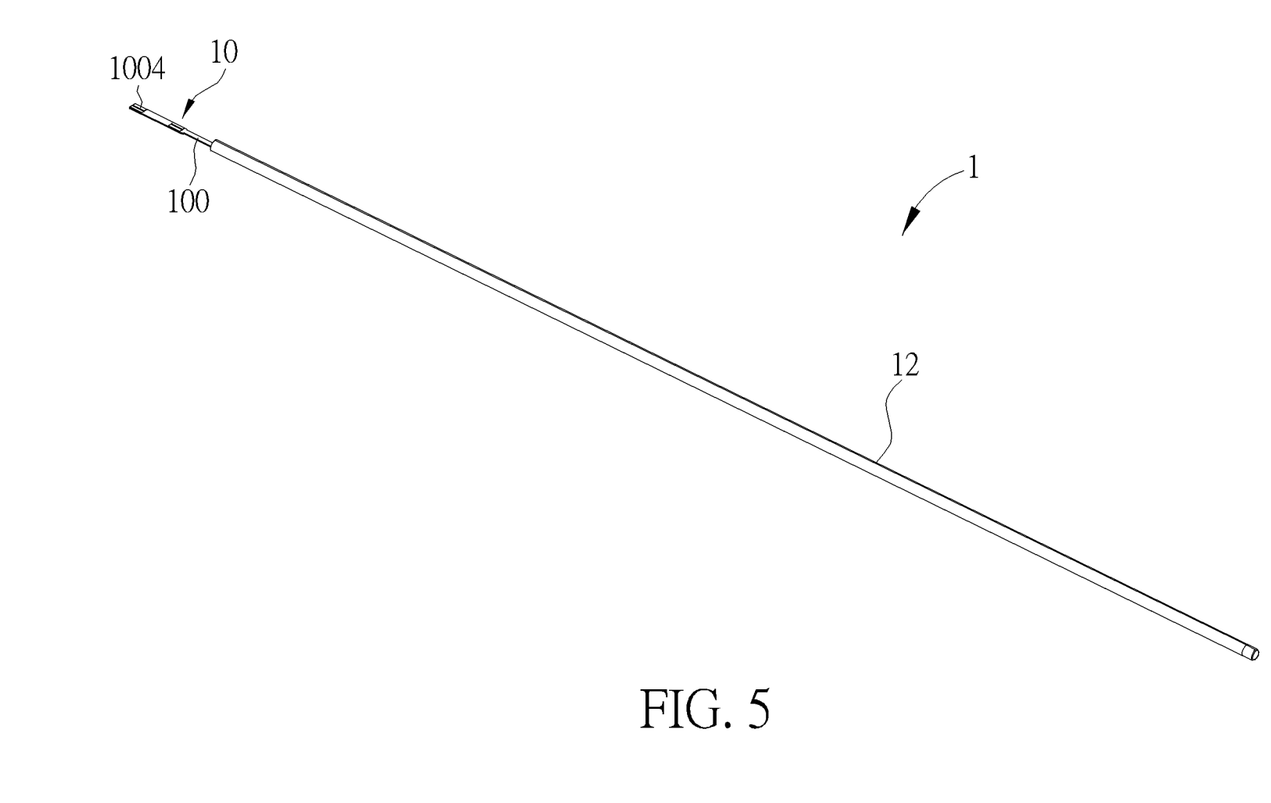
FIG. 5 is a perspective view illustrating an endoscope 1 equipped with the image capturing module shown in FIG. 4.
Figure 6:
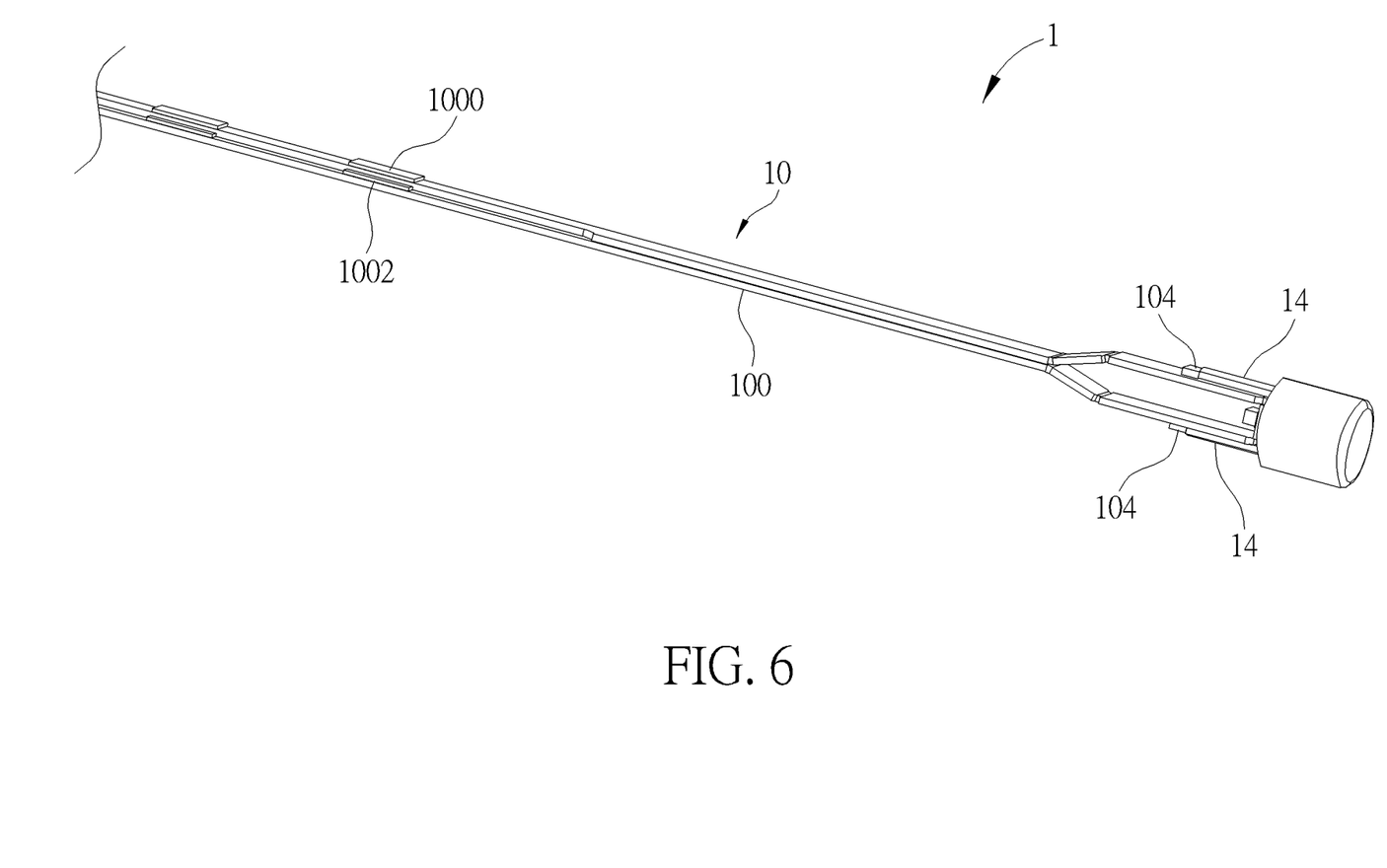
FIG. 6 is a perspective view illustrating the inside of the endoscope shown in FIG. 5.

Referring to FIGS. 5 and 6, FIG. 5 is a perspective view illustrating an endoscope 1 equipped with the image capturing module 10 shown in FIG. 4 and FIG. 6 is a perspective view illustrating the inside of the endoscope 1 shown in FIG. 5.

As shown in FIG. 5, an endoscope 1 comprises the aforesaid image capturing module 10 and a tube 12, wherein the image capturing module 10 is disposed in the tube 12. For further illustration, after the flexible circuit board 100 is folded and the first pads 1000 are welded with the second pads 1002, the folded flexible circuit board 100 with the image sensor 102 can be directly inserted into the elongated tube 12 to form the endoscope 1. As shown in FIG. 6, the endoscope 1 may further comprise a light guide structure 14 disposed in the tube 12. In this embodiment, the endoscope 1 may comprise two light guide structures 14 corresponding to the two light emitting units 104, but the invention is not so limited. After the image capturing module 10 is inserted into the tube 12, each of the light emitting units 104 is adjacent to the corresponding light guide structure 14, such that the light guide structure 14 is able to guide light emitted by the light emitting unit 104 out of the tube 12.

Figure 7:
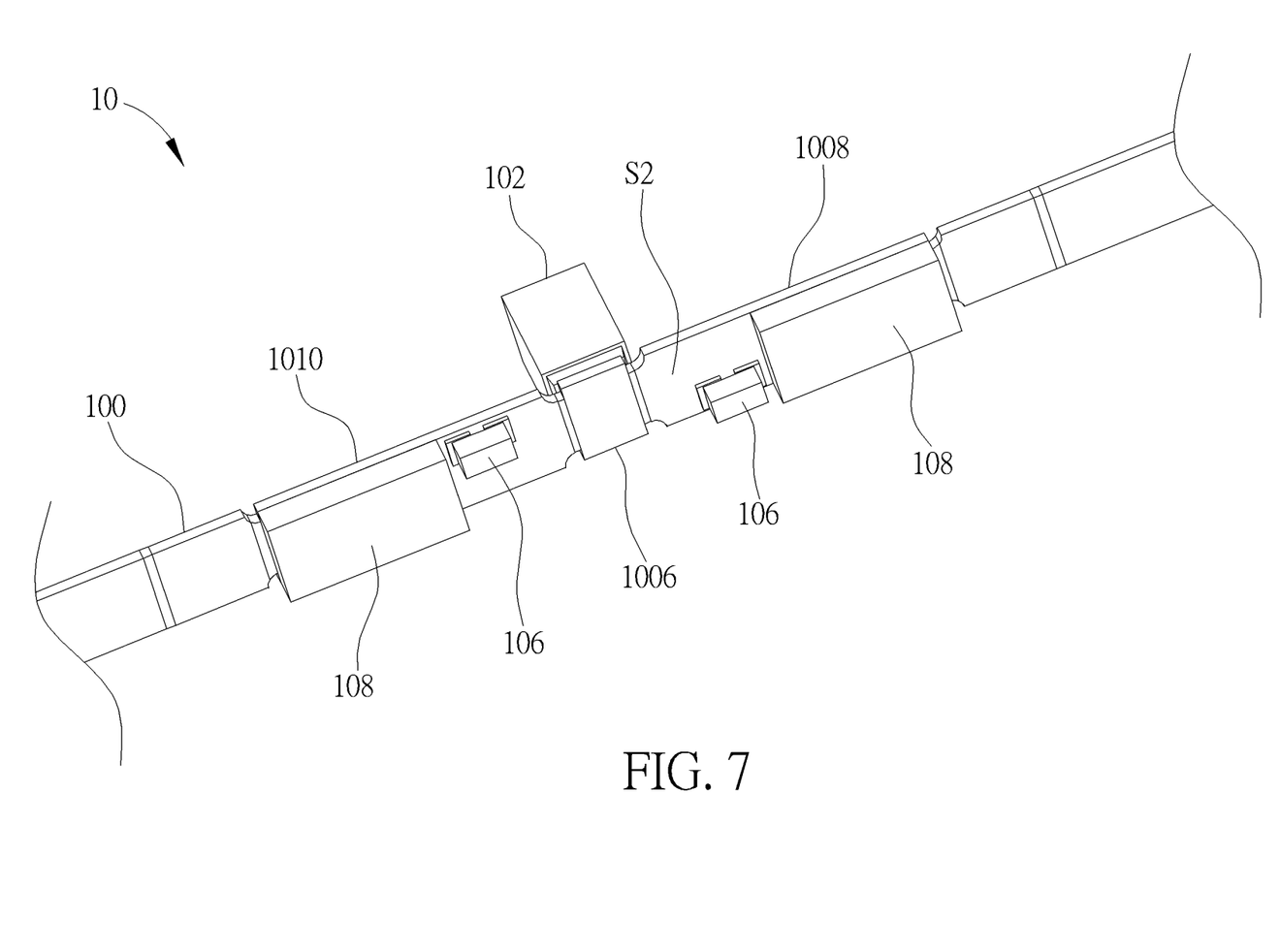
FIG. 7 is a perspective view illustrating parts of the image capturing module according to another embodiment of the invention.
Figure 8:
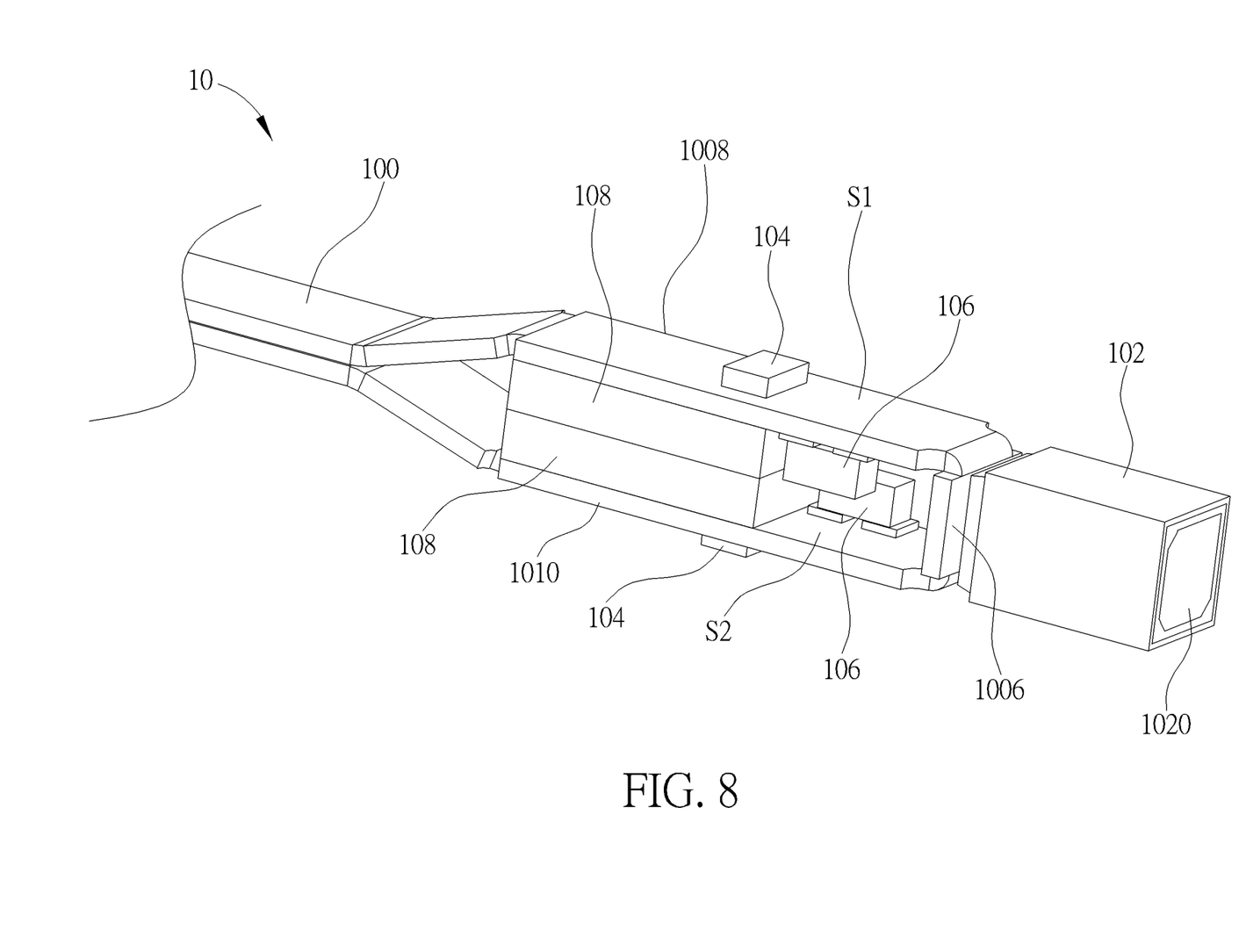
FIG. 8 is a perspective view illustrating the image capturing module shown in FIG. 7 after being folded.

Referring to FIGS. 7 and 8, FIG. 7 is a perspective view illustrating parts of the image capturing module 10 according to another embodiment of the invention and FIG. 8 is a perspective view illustrating the image capturing module 10 shown in FIG. 7 after being folded.

As shown in FIG. 7, the image capturing module 10 may further comprise two support members 108, wherein the two support members 108 are disposed on the second surface S2 of the flexible circuit board 100 and respectively located at the second folding segment 1008 and the third folding segment 1010. As shown in FIG. 8, after the flexible circuit board 100 is folded, the two support members 108 abut against each other, such that the light emitting unit 104 can be kept at a fixed position to avoid deviation. Furthermore, in this embodiment, the image capturing module 10 may comprise two electrical components 106, wherein the two electrical components 106 are disposed on the second surface S2 of the flexible circuit board 100 with respect to the two light emitting units 104. In other words, the two light emitting units 104 and the two electrical components 106 are disposed on opposite surfaces of the flexible circuit board 100. In another embodiment, the electrical component 106 may also be disposed on the first surface S1 of the flexible circuit board 100 with respect to the light emitting unit 104 and away from the image sensor 102, so as to avoid that the electrical component 106 occludes the light emitted by the light emitting unit 104 projecting out the tube 12. Therefore, the electrical component 106 may be disposed on at least one of the first surface S1 and the second surface S2 with respect to the light emitting unit 104.

Figure 9:
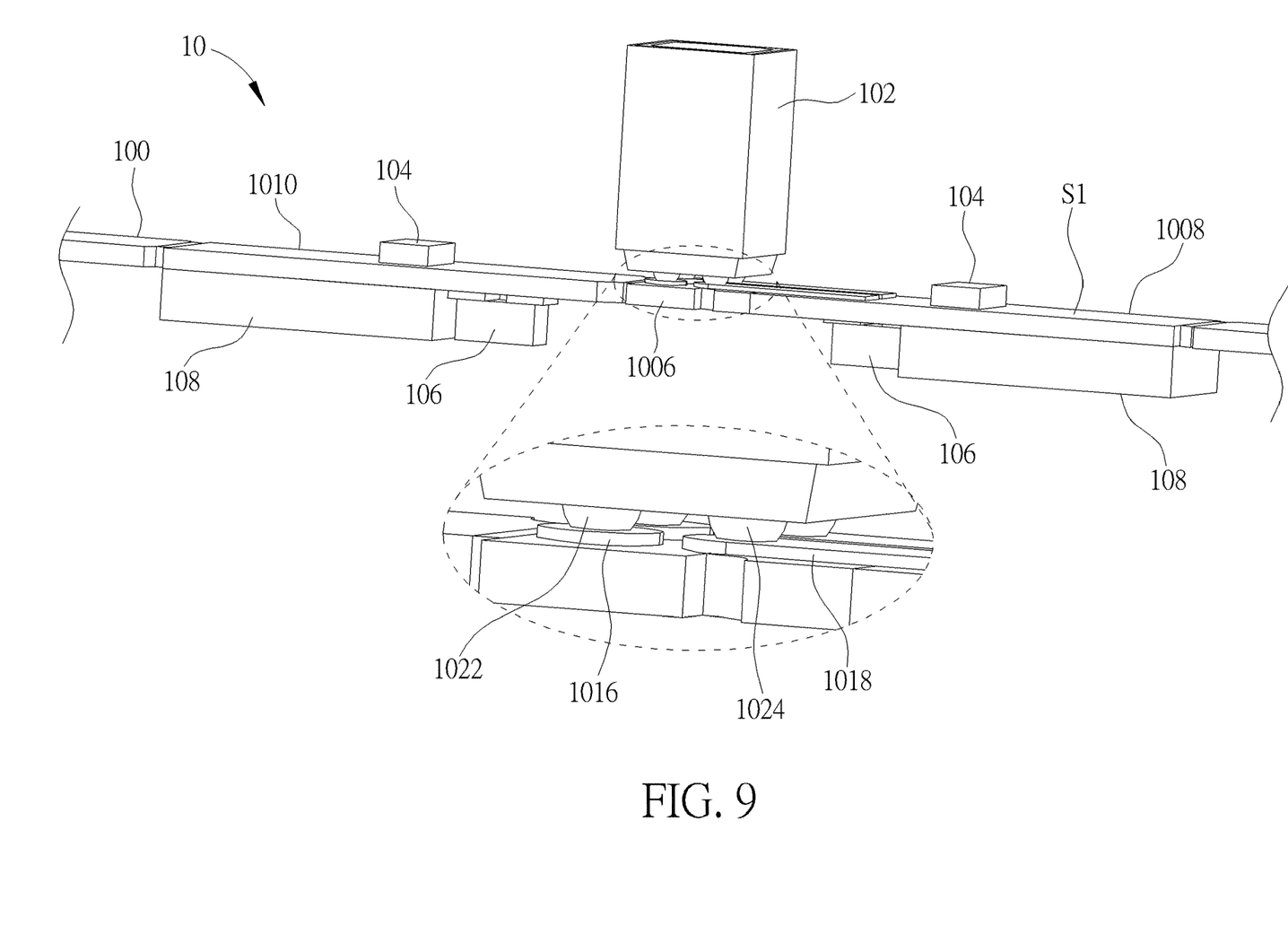
FIG. 9 is a perspective view illustrating parts of the image capturing module according to another embodiment of the invention.
Figure 10:
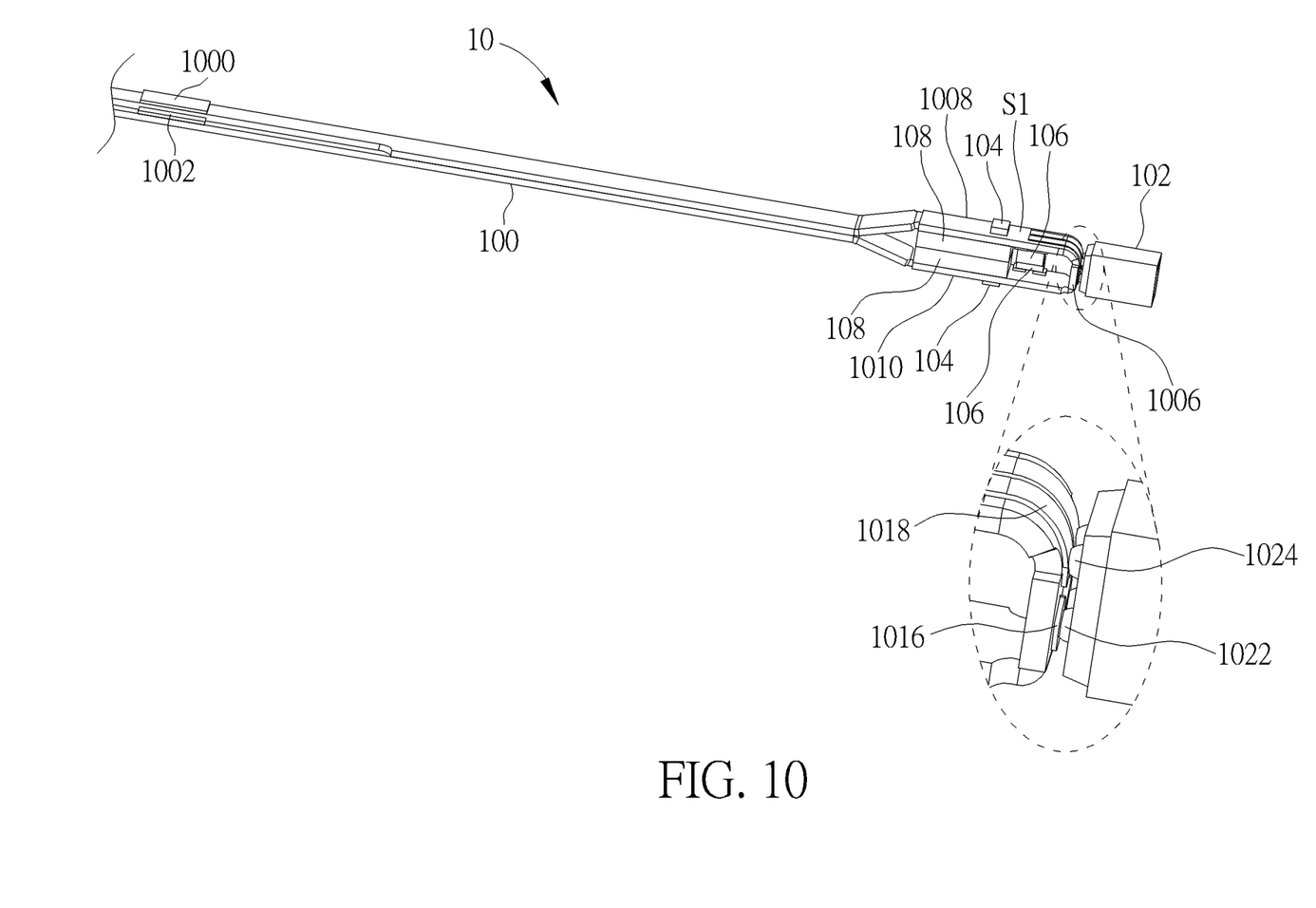
FIG. 10 is a perspective view illustrating the image capturing module shown in FIG. 9 after being folded.

Referring to FIGS. 9 and 10, FIG. 9 is a perspective view illustrating parts of the image capturing module 10 according to another embodiment of the invention and FIG. 10 is a perspective view illustrating the image capturing module 10 shown in FIG. 9 after being folded.

As shown in FIG. 9, the flexible circuit board 100 of the image capturing module 10 may further comprise at least two fourth pads 1016 and at least two fifth pads 1018 for connecting the image sensor 102. In this embodiment, the flexible circuit board 100 may comprise two fourth pads 1016 and two fifth pads 1018, but the invention is not so limited. The two fifth pads 1018 are longer than the two fourth pads 1016. Furthermore, the two fourth pads 1016 are located at the first folding segment 1006 and the two fifth pads 1018 extend from the first folding segment 1006 to the second folding segment 1008.

In this embodiment, before the flexible circuit board 100 is folded, two contacts 1022 of the image sensor 102 may be connected to the two fourth pads 1016 first by surface mount technology (SMT). Then, the flexible circuit board 100 is folded to align the first pads 1000 with the second pads 1002 and make alight receiving surface 1020 of the image sensor 102 perpendicular to surfaces of the first and second pads 1000, 1002. Then, the other two contacts 1024 of the image sensor 102 are welded to the two fifth pads 1018 on the first surface S1 of the flexible circuit board 100 while the first pads 1000 are welded with the second pads 1002. Since the two contacts 1024 of the image sensor 102 are welded to the flexible circuit board 100 after the flexible circuit board 100 is folded, the second folding segment 1008 may be folded closer to the third folding segment 1010, so as to further reduce the thickness of the folded flexible circuit board 100.

Figure 11:
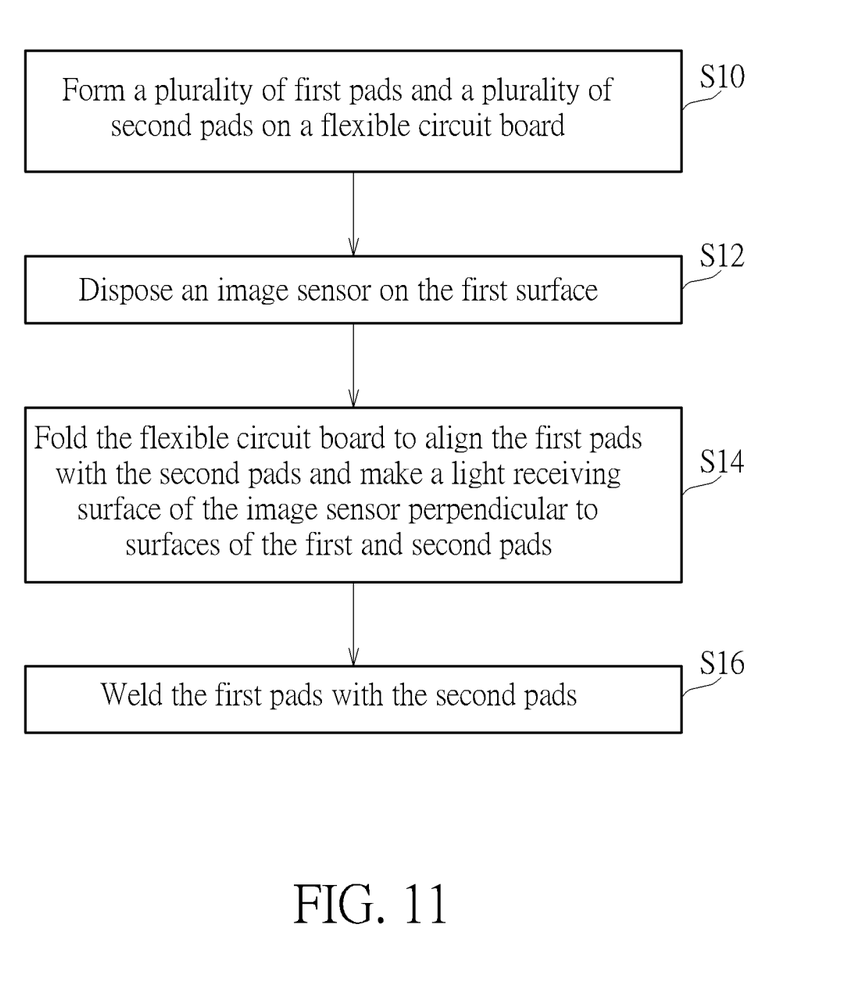
FIG. 11 is a flowchart illustrating a method of manufacturing the image capturing module according to an embodiment of the invention.

Referring to FIG. 11, FIG. 11 is a flowchart illustrating a method of manufacturing the image capturing module 10 according to an embodiment of the invention.

As shown in FIGS. 1 to 11, first, step S10 is performed to form a plurality of first pads 1000 and a plurality of second pads 1002 on a flexible circuit board 100, wherein the first pads 1000 is disposed on a first surface S1 of the flexible circuit board 100, the second pads 1002 is disposed on a second surface S2 of the flexible circuit board 100, and the first surface S1 is opposite to the second surface S2. Then, step S12 is performed to dispose an image sensor 102 on the first surface S1, wherein a distance D1 between the image sensor 102 and the first pads 1000 is identical to a distance D2 between the image sensor 102 and the second pads 1002. Then, step S14 is performed to fold the flexible circuit board 100 to align the first pads 1000 with the second pads 1002 and make a light receiving surface 1020 of the image sensor 102 perpendicular to surfaces of the first and second pads 1000, 1002. Then, step S16 is performed to weld the first pads 1000 with the second pads 1002.

In this embodiment, the step S12 may further comprise step of disposing at least one light emitting unit 104 on the first surface S1, wherein a distance D3 between the image sensor 102 and the at least one light emitting unit 104 is smaller than a distance d1 or D2 between the image sensor 102 and the first or second pads 1000, 1002.

According to the embodiments shown in FIGS. 1 to 4, 7 and 8, the step S12 may further comprise step of connecting the image sensor 102 to the first surface S1 of the flexible circuit board 100 by surface mount technology (SMT).

According to the embodiment shown in FIGS. 9 and 10, the step S12 may further comprise step of connecting at least two contacts 1022 of the image sensor 102 to the first surface S1 of the flexible circuit board 100 by surface mount technology (SMT), and the step S16 may further comprise step of welding at least two contacts 1024 of the image sensor 102 to the first surface S1 of the flexible circuit board 100.

It should be noted that the detailed embodiments of the method of manufacturing the image capturing module 10 of the invention are mentioned in the above and those will not be depicted herein again.

As mentioned in the above, the invention disposes the image sensor on the flexible circuit board first and then folds the flexible circuit board to weld the first pads with the second pads thereon. At this time, the light receiving surface of the image sensor is perpendicular to surfaces of the first and second pads. Accordingly, the folded flexible circuit board with the image sensor can be directly inserted into an elongated tube to form an endoscope, such that the method of manufacturing the endoscope can be simplified and the flexible circuit board of the invention can be used for installing a micro image sensor with small dimensions.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An image capturing module comprising:
 a flexible circuit board comprising a plurality of first pads and a plurality of second pads, the first pads being disposed on a first surface of the flexible circuit board, the second pads being disposed on a second surface of the flexible circuit board, the first surface being opposite to the second surface; and
 an image sensor disposed on the first surface, a distance between the image sensor and the first pads being identical to a distance between the image sensor and the second pads;
 wherein the flexible circuit board is folded, such that parts of the first surface and the second surface are located at an identical side to align and weld the first pads with the second pads and a light receiving surface of the image sensor is perpendicular to surfaces of the first and second pads.

2. The image capturing module of claim 1, wherein the first pads are located at a first portion of the flexible circuit board, the second pads are located at a second portion of the flexible circuit board, the second portion is connected to the first portion, and the first pads are wider than the second pads.

3. The image capturing module of claim 2, wherein the flexible circuit board further comprises a plurality of third pads for connecting a cable, the third pads are located at a third portion of the flexible circuit board, and the third portion is connected to the second portion.

4. The image capturing module of claim 3, wherein the third portion is wider than the second portion.

5. The image capturing module of claim 1, further comprising at least one light emitting unit disposed on the first surface, a distance between the image sensor and the at least one light emitting unit being smaller than either the distance between the image sensor and the first pads or the distance between the image sensor and the second pads.

6. The image capturing module of claim 5, wherein the flexible circuit board comprises a first folding segment, a second folding segment and a third folding segment, the first folding segment is connected between the second folding segment and the third folding segment, the image sensor is located at the first folding segment, the at least one light emitting unit is located at at least one of the second folding segment and the third folding segment, and the first folding segment is perpendicular to the second folding segment and the third folding segment.

7. The image capturing module of claim 6, further comprising two support members respectively located at the second folding segment and the third folding segment, the two support members being disposed on the second surface and abutting against each other.

8. The image capturing module of claim 6, wherein joints between the first folding segment, the second folding segment and the third folding segment have rounded recess structures.

9. The image capturing module of claim 6, wherein the flexible circuit board further comprises at least two fourth pads and at least two fifth pads for connecting the image sensor, the at least two fifth pads are longer than the at least two fourth pads, the at least two fourth pads are located at the first folding segment, and the at least two fifth pads extend from the first folding segment to the second folding segment.

10. The image capturing module of claim 1, further comprising at least one electrical component disposed on the second surface with respect to the image sensor.

11. The image capturing module of claim 5, further comprising at least one electrical component disposed on at least one of the first surface and the second surface with respect to the at least one light emitting unit.

12. An endoscope comprising:
 a tube; and
 an image capturing module disposed in the tube, the image capturing module comprising:
  a flexible circuit board comprising a plurality of first pads and a plurality of second pads, the first pads being disposed on a first surface of the flexible circuit board, the second pads being disposed on a second surface of the flexible circuit board, the first surface being opposite to the second surface; and
  an image sensor disposed on the first surface, a distance between the image sensor and the first pads being identical to a distance between the image sensor and the second pads;
  wherein the flexible circuit board is folded, such that parts of the first surface and the second surface are located at an identical side to align and weld the first pads with the second pads and a light receiving surface of the image sensor is perpendicular to surfaces of the first and second pads.

13. The endoscope of claim 12, further comprising a light guide structure disposed in the tube, at least one light emitting unit being adjacent to the light guide structure.

14. The endoscope of claim 12, wherein the first pads are located at a first portion of the flexible circuit board, the second pads are located at a second portion of the flexible circuit board, the second portion is connected to the first portion, and the first pads are wider than the second pads.

15. The endoscope of claim 12, wherein the image capturing module further comprises at least one light emitting unit disposed on the first surface, a distance between the image sensor and the at least one light emitting unit is smaller than either the distance between the image sensor and the first pads or the distance between the image sensor and the second pads.

16. The endoscope of claim 15, wherein the flexible circuit board comprises a first folding segment, a second folding segment and a third folding segment, the first folding segment is connected between the second folding segment and the third folding segment, the image sensor is located at the first folding segment, the at least one light emitting unit is located at at least one of the second folding segment and the third folding segment; after the flexible circuit board is folded, the second folding segment is parallel to the third folding segment, and the first folding segment is perpendicular to the second folding segment and the third folding segment.

17. The endoscope of claim 16, wherein the image capturing module further comprises two support members respectively located at the second folding segment and the third folding segment, the two support members are disposed on the second surface and abut against each other.

18. The endoscope of claim 16, wherein joints between the first folding segment, the second folding segment and the third folding segment have rounded recess structures.

19. The endoscope of claim 16, wherein the flexible circuit board further comprises at least two fourth pads and at least two fifth pads for connecting the image sensor, the at least two fifth pads are longer than the at least two fourth pads, the at least two fourth pads are located at the first folding segment, and the at least two fifth pads extend from the first folding segment to the second folding segment.

20. The image capturing module of claim 1, wherein the image sensor is connected to the first surface of the flexible circuit board by surface mount technology.

* * * * *